United States Patent
Vallana

(10) Patent No.: US 11,679,001 B2
(45) Date of Patent: Jun. 20, 2023

(54) INTERSOMATIC CAGE FOR VERTEBRAL STABILIZATION

(71) Applicant: SPS S.r.l., Scarmagno (IT)

(72) Inventor: Valerio Vallana, Turin (IT)

(73) Assignee: SPS S.r.l., Scarmagno (IT)

( * ) Notice: Subject to any disclaimer, the term of this patent is extended or adjusted under 35 U.S.C. 154(b) by 0 days.

(21) Appl. No.: 17/349,979

(22) Filed: Jun. 17, 2021

(65) Prior Publication Data

US 2021/0393417 A1 Dec. 23, 2021

(30) Foreign Application Priority Data

Jun. 18, 2020 (IT) .......................... 102020000014569

(51) Int. Cl.
*A61F 2/44* (2006.01)
*A61F 2/30* (2006.01)

(52) U.S. Cl.
CPC .............. *A61F 2/447* (2013.01); *A61F 2/442* (2013.01); *A61F 2002/30677* (2013.01); *A61F 2002/30772* (2013.01); *A61F 2310/00023* (2013.01); *A61F 2310/00179* (2013.01)

(58) Field of Classification Search
CPC .......... A61F 2/44; A61F 2/4455; A61F 2/447; A61F 2002/30677–3068; A61F 2002/30772
See application file for complete search history.

(56) References Cited

U.S. PATENT DOCUMENTS

| | | | |
|---|---|---|---|
| 2006/0093646 A1* | 5/2006 | Cima ...................... | A61L 27/54 606/76 |
| 2008/0221681 A1* | 9/2008 | Trieu ................... | A61F 2/30767 29/592 |
| 2010/0152857 A1* | 6/2010 | Freeman ................. | A61F 2/447 623/17.16 |
| 2014/0288650 A1* | 9/2014 | Hunt .................... | A61F 2/30907 623/16.11 |
| 2019/0133783 A1* | 5/2019 | Unger ................. | A61F 2/30771 |
| 2019/0282367 A1 | 9/2019 | Casey et al. | |
| 2019/0343644 A1* | 11/2019 | Ryan ................... | A61F 2/30771 |
| 2019/0343652 A1 | 11/2019 | Petersheim et al. | |
| 2020/0093612 A1 | 3/2020 | Blain et al. | |
| 2020/0214852 A1* | 7/2020 | Tipping .................. | A61F 2/447 |
| 2020/0276019 A1* | 9/2020 | Shetty ................... | A61F 2/4455 |
| 2020/0297505 A1* | 9/2020 | McLaughlin ......... | A61F 2/4465 |

FOREIGN PATENT DOCUMENTS

| | | |
|---|---|---|
| CN | 205515049 U | 8/2016 |
| CN | 107349034 A | 11/2017 |
| CN | 109730814 A | 5/2019 |
| EP | 3406226 A1 | 11/2018 |
| EP | 3459502 A1 | 3/2019 |
| FR | 3050927 A1 | 11/2017 |

OTHER PUBLICATIONS

Italian Search Report dated Mar. 2, 2021. 9 pages.

* cited by examiner

Primary Examiner — Eduardo C Robert
Assistant Examiner — Michelle C Eckman
(74) Attorney, Agent, or Firm — RMCK Law Group PLC

(57) ABSTRACT

Intersomatic cage for vertebral stabilization, including a generally prismatic body having an outer rigid framework in the form of a truss within which at least one insert incorporating slow prolonged release substances selected from the classes of anti-inflammatory, anti-infection and bone regrowth promoter drugs is housed.

5 Claims, 2 Drawing Sheets

INTERSOMATIC CAGE FOR VERTEBRAL STABILIZATION

CROSS-REFERENCE TO RELATED APPLICATION

This application claims priority to Italian Patent Application No. 102020000014569 filed Jun. 18, 2020. The disclosure of the above application is incorporated herein by reference in its entirety.

FIELD OF THE INVENTION

The present invention relates to an intersomatic cage for vertebral stabilization designed to be inserted between two contiguous vertebrae so as to space them apart and thus keep them at a mutual distance such to restore the intervertebral space, creating the decompression of the nerve roots and the acceleration of the intersomatic fusion.

STATE OF THE PRIOR ART

Intersomatic cages thus made comprise a generally prismatic-shaped body provided with a nose protruding from the front end of the body and designed to be inserted between two contiguous vertebrae during the surgical insertion of the intersomatic cage.

Distinctive examples of intersomatic cages for vertebral stabilization are described and illustrated, for example, in Italian patent applications no. 102019000023913 and no. 102020000001210 on behalf of the Applicant in question, not published at the filing or priority date of the present application.

These cages are applied using invasive surgical techniques which typically provide for—following insertion of the nose between the two vertebrae—rotations alternately in the direction of the cage and in the opposite direction, performed by means of a suitable manual instrument, while it is pushed so as to be wedged between the vertebrae.

Following the application, the intervertebral region is normally subject to inflammations and also to infections in some cases. Bone regrowth may also be insufficient and unsuitable to effectively incorporate the cage over time.

Documents US2019/343652 and FR 3050927 disclose cages for vertebral stabilization incorporating slow prolonged release substances selected for example from the classes of anti-inflammatory, anti-infection and bone regrowth promoter drugs.

SUMMARY OF THE INVENTION

The object of the present invention is to provide an intersomatic cage that allows to improve the functional effectiveness of the aforementioned substances significantly limiting if not even eliminating the clinical consequences for patients following the application thereof.

According to the invention, this object is achieved essentially due to the fact that the body of the intersomatic cage comprises an outer rigid framework defining wide apertures and in which at least one insert incorporating the aforementioned substances is housed, said rigid framework consisting of a truss arranged at the upper, lower and side faces of the prismatic body.

Preferably, the framework is made of titanium or of a similar biocompatible material, and the body containing the prolonged release drugs may consist of a spongy or filamentous or porous material, and also of ceramic materials filled with nanoparticles.

BRIEF DESCRIPTION OF THE DRAWINGS

The invention will now be described in detail with reference to the attached drawings, provided purely by way of non-limiting example, wherein.

DETAILED DESCRIPTION OF THE INVENTION

Figure 1:
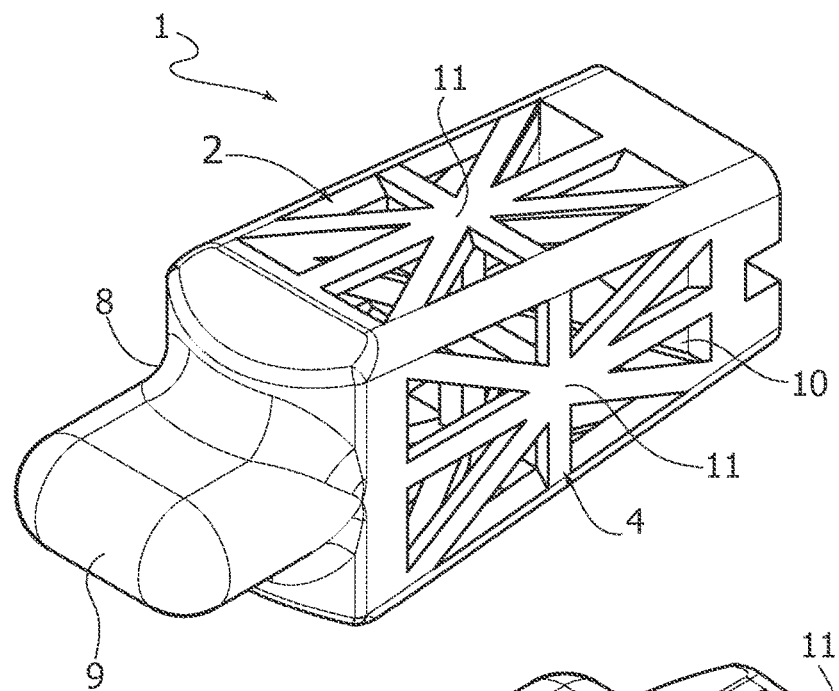
FIG. 1 is a front perspective view of the intersomatic cage according to the invention.
Figure 2:
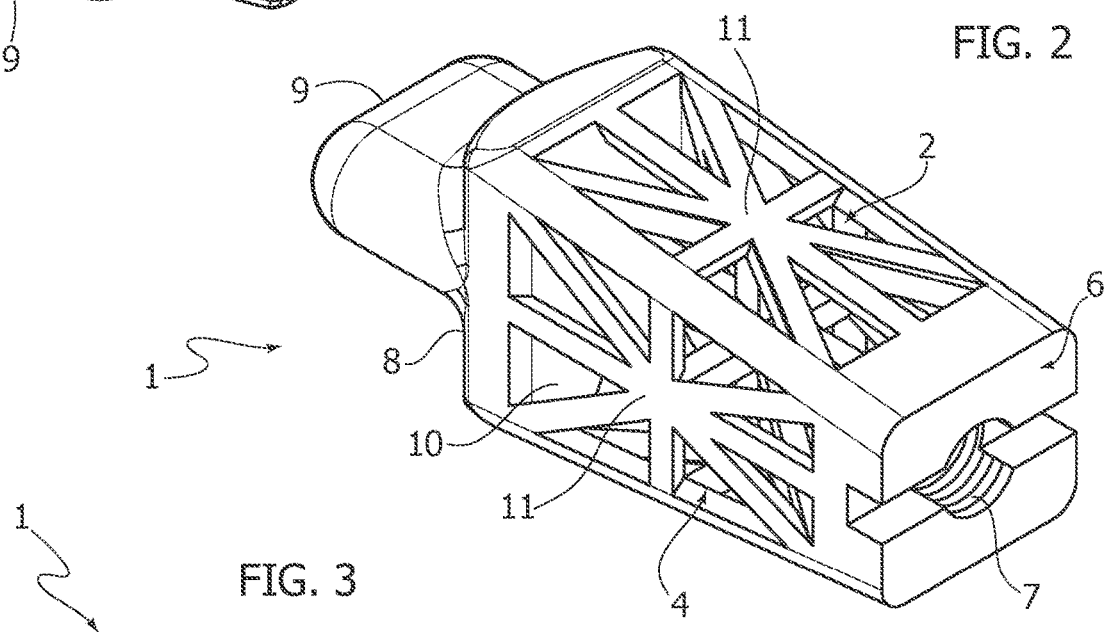
FIG. 2 is a dorsal perspective view of the cage.
Figure 3:
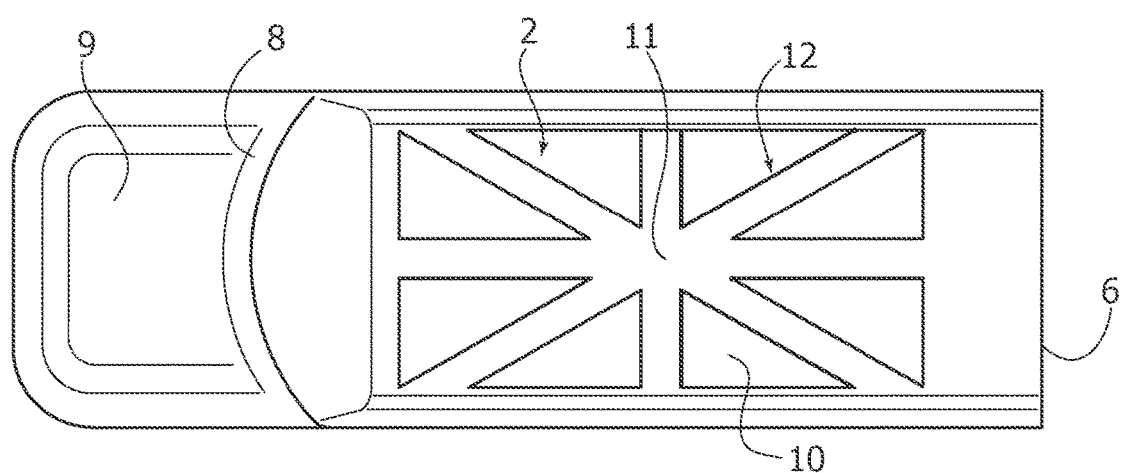
FIG. 3 is a top plan view of the cage.
Figure 4:
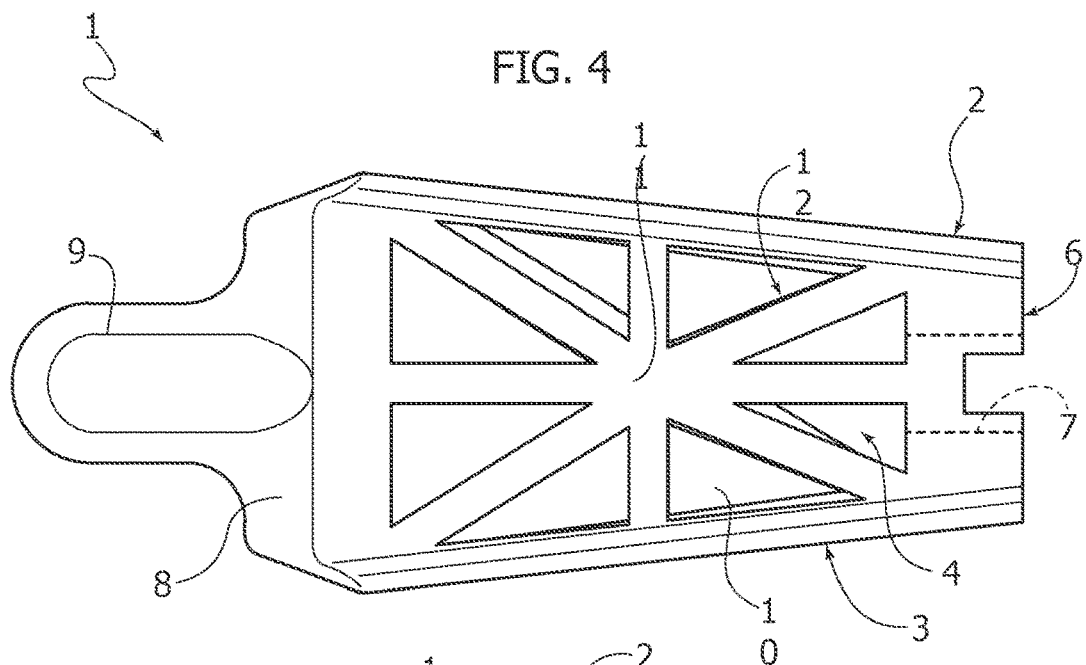
FIG. 4 is a side elevational view of the cage.
Figure 5:
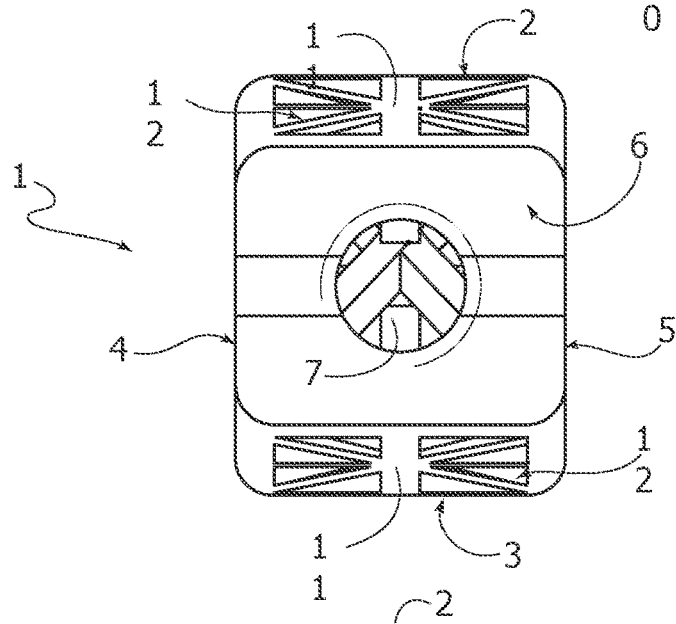
FIG. 5 is a front elevational view of FIG. 4.
Figure 6:
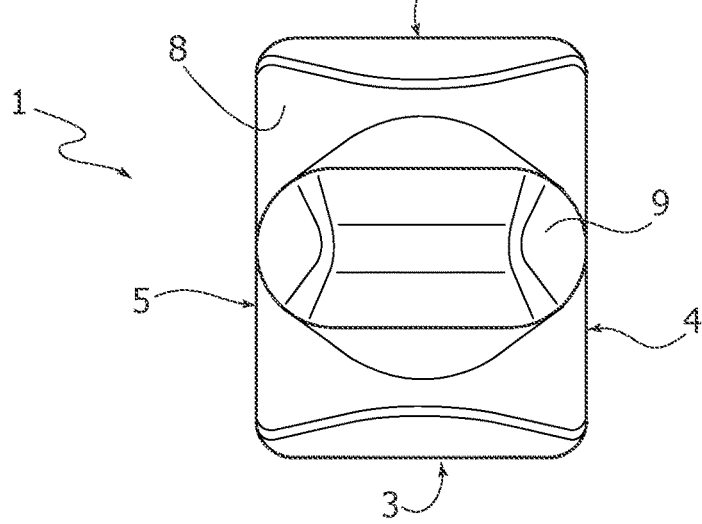
FIG. 6 is a dorsal elevational view of FIG. 4.

With reference to the figures, the intersomatic cage according to the invention consists of a generally prismatic-shaped and more precisely parallelepiped-shaped monolithic body 1, having an upper face 2 and a lower face 3 (with reference to the implanted position of the cage in the intervertebral space of a subject with an upright spine), and side faces 4, 5.

A recess 7 for introducing a tool for the surgical insertion of the cage into the intervertebral space is formed on the rear face of the body 1, indicated with 6. This instrument, not illustrated, is configured so as to engage axially and torsionally with the recess 7 so as to be able to rotate the body 1 alternately in a clockwise and anti-clockwise direction or vice versa while being simultaneously pushed.

A nose 9—which has the function of paving the way by dilating the intervertebral space during the process for inserting the intersomatic cage—protrudes from the front end of the body 1, indicated with reference numeral 8.

The shape of the nose 9 is conveniently similar to that described and illustrated in the previously cited Italian patent application n° 102019000023913 on behalf of the Applicant in question, not published at the filing or priority date of the present application.

According to the distinctive characteristic of the invention, the body 1 is hollow and it consists—at the upper, 2 lower 3 and side 4, 5 faces thereof (with reference to the implanted condition of the cage in a subject in an upright position)—of a truss defining an outer rigid framework 11 with wide openings that place the cavity thereof in communication with the external.

The framework 11 with truss, which—as mentioned—is provided at all faces 2, 3, 4, 5, consists of coplanar rods which are rigidly constrained to each other and to the faces 7, 8 so as to form a strong and undeformable structure.

The body is made of a biocompatible material, for example titanium, and it is for example made by means of additive techniques of the powder sintering type. Other conventional manufacturing techniques can of course be envisaged.

According to another distinctive characteristic of the invention, an insert 10 incorporating or soaked with slow prolonged release pharmacological substances selected from the classes of anti-inflammatory, anti-infection and bone regrowth promoter drugs is housed in the body of the cavity. The insert 10 may have a spongy or filamentous or porous structure, in this case for example it may also be obtained by means of additive techniques, or it can also consist of ceramic materials filled with nanoparticles. It can be made of a single piece divided into distinct areas for the different pharmacological substances, or it can consist of independent and separate sectors, each incorporating the respective drug.

Typically the pharmacological substances can be the following:

Growth promoters: drugs also with multimodal action, combining chemotactic, mitogenic, morphogenic, metabolic or apoptotic factors. They include BMPs (bone morphogenetic proteins), in particular BMP-2 and BMP-7; VEGFs (vascular endothelial growth factors), which have been studied to promote the growth of blood vessels for the vascularisation of the bone; fibroblast growth factors. The use of statins has also been shown to promote the expression of BMP-2 in mRNA in osteoblasts.

Anti-infection: primarily broad spectrum antibiotics such as gentamicin and vancomycin Usual anti-inflammatory agents.

These substances are then normally added to excipients of various conventional types, also suitable to facilitate the slow release thereof.

The truss-like conformation of the framework 11 allows to significantly improve the gradual and homogeneous release of the aforementioned slow prolonged release pharmacological substances, ultimately improving the functional effectiveness of the cage according to the invention for the effects of such release.

Obviously, the construction details and the embodiments may widely vary with respect to what has been described and illustrated, without departing from the scope of protection of the invention as described in the claims that follow.

The invention claimed is:

1. An intersomatic cage for vertebral stabilization, comprising:
    a generally prismatic body having four outer faces and a protruding nose extending therefrom, and configured to be inserted between two contiguous vertebrae so as to space them apart during a surgical insertion of the cage,
    wherein the four outer faces of the body include an upper face, a lower face and two side faces connecting the upper and lower faces,
    wherein the body defines a body opening in each outer face that extends over at least a majority of that outer face,
    wherein the body includes an outer rigid framework consisting of a truss structure arranged in the body opening of each face and forming the upper, lower and side faces of the body,
    wherein the truss structure defines wide apertures within the body opening of each outer face, and within which at least one insert incorporating slow prolonged release substances selected from the classes of anti-inflammatory, anti-infection and bone regrowth promoter drugs is housed.

2. The intersomatic cage according to claim 1, wherein the framework is made of titanium.

3. The intersomatic cage according to claim 1, wherein said at least one insert is made of a spongy or filamentous or porous material.

4. The intersomatic cage according to claim 1, wherein said at least one insert consists of ceramic materials filled with nanoparticles.

5. The intersomatic cage according to claim 1, wherein the body opening includes an outer perimeter, and wherein the truss structure consists of coplanar rods rigidly constrained to each other and the perimeter of the body opening.

* * * * *